United States Patent [19]

Stubbe

[11] Patent Number: 4,720,572

[45] Date of Patent: Jan. 19, 1988

[54] PROCESS FOR THE PREPARATION OF 4-ACYLOXY-3-OXO-BUTYRIC ACID ESTERS

[75] Inventor: Mathias Stubbe, Wuppertal, Fed. Rep. of Germany

[73] Assignee: Bayer Aktiengesellschaft, Leverkusen, Fed. Rep. of Germany

[21] Appl. No.: 798,526

[22] Filed: Nov. 15, 1985

[30] Foreign Application Priority Data

Nov. 30, 1984 [DE] Fed. Rep. of Germany ....... 3443678

[51] Int. Cl.⁴ .............................................. C07C 69/76
[52] U.S. Cl. ..................... 560/104; 560/174; 560/236; 560/112
[58] Field of Search .............. 560/174, 104, 236, 112

[56] References Cited

U.S. PATENT DOCUMENTS 2,376,033  5/1945  Clifford ............................... 560/174
3,998,815  12/1976  Bodor ................................. 560/104
4,335,251  6/1982  Noda .................................... 560/105

FOREIGN PATENT DOCUMENTS 2024948  1/1971  Fed. Rep. of Germany ...... 560/236

OTHER PUBLICATIONS

Chemical Abstracts, vol. 97, 1982-p. 768.

*Primary Examiner*—Paul J. Killos
*Attorney, Agent, or Firm*—Sprung Horn Kramer & Woods

[57] ABSTRACT

A process for the preparation of a 4-acyloxy-3-oxo-butyric acid ester of the formula

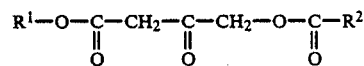

in which
  $R^1$ is alkyl with up to 4 C atoms, and
  $R^2$ is alkyl with up to 4 C atoms and optionally substituted by halogen, hydroxyl, alkoxy or phenyl, or is aryl,
which comprises reacting a 4-halogenobutyric acid ester of the formula

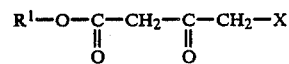

in which X is chlorine or bromine, with a carboxylic acid of the formula

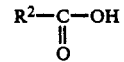

in the presence of acid-trapping agent in an organic solvent at a temperature of between 0° and 170° C.

5 Claims, No Drawings

PROCESS FOR THE PREPARATION OF 4-ACYLOXY-3-OXO-BUTYRIC ACID ESTERS

The invention relates to a new process for the preparation of 4-acyloxy-3-oxo-butyric acid esters, some of which are known, which can be used for the preparation of pharmaceutically active compounds.

All the processes known hitherto are either expensive or unacceptable for safety and ecological reasons (compare I. Ratusky, F. Sorm, Chem. Listy 51, 1091–1100 (1957); J. I. De Graw, Tetrahedron 28, 967–972 (1972); and A. L. Veresh chogin, A. A. Semenow, Zh. Org. Khim 18, 1772/3 (1982)).

It has now been found that the 4-acyloxy-3-oxobutyric acid esters of the general formula (I)

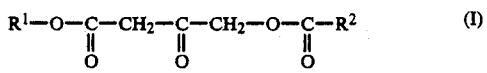     (I)

in which
   $R^1$ represents straight-chain or branched alkyl with up to 4 C atoms, preferably methyl or ethyl, and
   $R^2$ represents straight-chain or branched alkyl with up to 4 C atoms (optionally substituted by halogen, hydroxyl, alkoxy or phenyl), preferably with up to 2 C atoms, and particularly preferably methyl, or represents aryl, preferably phenyl,
are obtained by a process in which 4-halogenobutyric acid esters of the general formula (II)

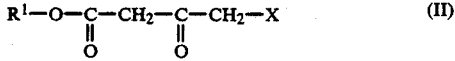     (II)

in which
   $R^1$ has the abovementioned meaning and
   X represents chlorine or bromine, preferably chlorine,
are reacted with carboxylic acids of the general formula (III)

     (III)

in which $R^2$ has the abovementioned meaning, in the presence of acid-trapping agents in aprotic organic solvents.

Surprisingly, the process according to the invention gives the end product in good yields not only when the bromine derivatives are used but also when the chlorine derivatives of the compound (II) are used. In addition, working up and purification of the end products are easy to carry out industrially.

The compounds of the formula (I) obtainable according to the invention are particularly suitable for the preparation of 1,4-dihydropyridines which carry a lactone ring in the 2- and 3-position. The preparation is carried out, for example, by reacting compounds of the formula (I) with aldehydes and if appropriate after the ylidene compounds formed have been isolated, with aminocrotonic acid esters to give the corresponding dihydropyridines (compare DE-OS (German Published Specification) No. 3,206,671).

If methyl 4-chloro-3-oxo-butyrate and acetic acid are used as starting substances, the course of the reaction can be illustrated by the following equation:

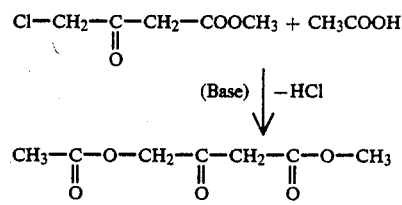

The starting substances are known or can be prepared by known processes.

Possible solvents are all the protic and aprotic organic solvents. These include halogenated hydrocarbons, such as methylene chloride, chloroform and trichloroethylene, ethers, such as diethyl ether, dioxane, tetrahydrofuran or glycol monomethyl or glycol dimethyl ether, hydrocarbons, such as toluene or xylene, secondary and tertiary alcohols, such as isopropanol, 2-butanol and tert.-butanol, dimethylformamide, methyl isobutyl ketone or acetonitrile. Preferred solvents are toluene, dimethylformamide and methyl isobutyl ketone.

Possible acid-trapping agents are the customary organic bases. These include tertiary and secondary alkylamines, pyridine or piperidine. Triethylamine is particularly preferred.

The reaction is carried out at temperatures of 0°–170° C., preferably at temperatures of 60°–120° C. If appropriate, it has proved advantageous to carry out the reaction at the boiling point of the solvent used.

The reaction can be carried out under normal or increased pressure. In general, it is carried out under normal pressure.

In carrying out the process according to the invention, 1–5 moles, preferably 1–2.5 moles, of the carboxylic acid of the formula (III) are employed per mole of the halogen compound of the formula (II). 0.5–1.5 moles of acid-trapping agent are in turn employed per mole of the carboxylic acid of the formula (III). If appropriate, it is also possible to use the ammonium salts of the carboxylic acids.

The products can be purified very simply by extraction of the water-soluble constituents and subsequent distillation or crystallization.

EXAMPLE 1

Ethyl 4-acetoxy-3-oxobutyrate

A solution of 1.204 l (21.0 moles) of glacial acetic acid and 2.786 l (20.0 moles) of triethylamine in 8.75 l of methyl isobutyl ketone is heated under reflux, and a solution of 1.498 l (11.2 moles) of ethyl 4-chloro-3-oxobutyrate in 1.75 l of methyl isobutyl ketone is added at the boiling point in the course of 20 minutes. When the addition has ended, the mixture is heated under reflux for a further 30 minutes and cooled to about 5° C. and the salts which have precipitated out are filtered off. The residue on the filter is washed with 4.5 l of methyl isobutyl ketone. The combined filtrates are concentrated in vacuo, and first 2 l of drinking water and then 4 l of a 9% strength sodium bicarbonate solution are added to the residue. The suspension is extracted three times with 4 l of ethyl acetate each time and the combined extracts are dried over 2 kg of sodium sulphate, filtered and concentrated in a rotary evaporator at a bath temperature of 40° C.

The residue is subjected to fractional distillation.

Yield: 885 g (42% of theory)

Boiling point: 84°–86° C./0.4 mm Hg

EXAMPLE 2

Ethyl 4-acetoxy-3-oxobutyrate 71 ml of ethyl 4-chloro-3-oxobutyrate are reacted with 57 ml of acetic acid and 132 ml of triethylamine in 1 l of dimethylformamide by the procedure described in Example 1.

Yield: 43.2 g (43.3% of theory)

EXAMPLE 3

Ethyl 4-acetoxy-3-oxobutyrate 71 ml of ethyl 4-chloro-3-oxobutyrate are reacted with 57 ml of acetic acid and 132 ml of triethylamine in 1 l of 2-butanol by the procedure described in Example 1.

Yield: 42.4 g (42.5% of theory)

EXAMPLE 4

Ethyl 4-propionyloxy-3-oxobutyrate

A solution of 71 ml of ethyl 4-chloro-3-oxobutyrate in 165 ml of toluene is added to a boiling solution of 73 ml of propionic acid and 132 ml of triethylamine in 833 ml of toluene in the course of 30 minutes. The mixture is boiled under reflux for 90 minutes and then cooled, the triethylamine hydrochloride which has precipitated out is filtered off with suction and extracted twice with 300 ml of water each time and the solvent is distilled off in vacuo. The residue is subjected to fractional distillation under a high vacuum.

Yield: 48.0 g (44.8% of theory)

$C_9H_{14}O_5$ (202.2) calculated: C 53.5; H 6.6; O 39.6; found: C 53.2; H 6.9; O 39.8.

EXAMPLE 5

Ethyl 4-benzyloxy-3-oxobutyrate 71 ml of ethyl 4-chloro-3-oxobutyrate are reacted with 121.4 g of benzoic acid and 132 ml of triethylamine in 1 l of toluene by the procedure described in Example 4. After removal of the solvent by distillation, the residue is a virtually pure product.

Yield: 118.3 g (89% of theory)

$C_{13}H_{14}O_5$ (250.3) calculated: C 62.4; H 5.6; O 32.0; found: C 62.7; H 5.5; O 31.8.

$^1$H-NMR (250 MHz, CdCl$_3$) $\delta = 1.30$ (t, 3H; CH$_2$-CH$_3$) 3.52 (S, 2H; 2-H), 4.24 (q, 2H; O-CH$_2$-CH$_3$), 5.60 (S, 2H; 4-H), 7.52 (t, 2H; 3',5'-H), 7.66 (t, 1H; 4'-H), and 8.14 (d, 2H; 2',6'-H).

EXAMPLE 6

Ethyl 4-(methoxyacetoxy)-3-oxobutyrate 71 ml of ethyl 4-chloro-3-oxo-butyrate are reacted with 89.5 g of methoxyacetic acid and 132 ml of triethylamine in 1 l of toluene by the procedure described in Example 4. The product is purified by bulb tube distillation.

Yield: 44.3 g (38.3% of theory)

$C_9H_{14}O_6$ (218.2) calculated: C 49.5; H 6.5; O 44.0; found: C 49.8; H 6.6; O 43.7.

$^1$H-NMR (250 MHz, COCl$_3$) $\delta = 1.27$ (t, 3H, O-CH$_2$-CH$_3$) 3.47 (S, 3H, O-CH$_3$), 3.50 (S, 2H, 2-H), 4.14 (S, 2H, CO-CH$_2$-O-CH$_3$), 4.24 (q, 2H, O-CH$_2$-CH$_3$) and 4.90 (S, 2H, 4-H)

It is understood that the specification and examples are illustrative but not limitative of the present invention and that other embodiments within the spirit and scope of the invention will suggest themselves to those skilled in the art.

I claim:

1. A process for the preparation of a 4-acyloxy-3-oxobutyric acid ester of the formula

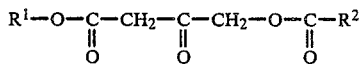

in which $R^1$ is alkyl with up to 4 C atoms, and $R^2$ is alkyl with up to 4 C atoms and optionally substituted by halogen, hydroxyl, alkoxy or phenyl, or is aryl, which comprises reacting a 4-halogenobutyric acid ester of the formula

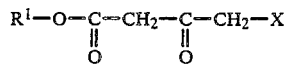

in which

X is chlorine or bromine, with a carboxylic acid of the formula

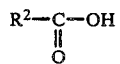

in the presence of at least one of a secondary or tertiary alkylamine, pyridine, piperidine or an ammonium salt of a carboxylic acid as an acid-trapping agent in an organic solvent at a temperature between 0° and 170° C.

2. A process according to claim 1, in which $R^1$ is methyl or ethyl and $R^2$ is alkyl with up to 4 C atoms and optionally substituted by fluorine, chlorine bromine, hydroxyl, alkoxy with 1 or 2 C atoms or phenyl, or is phenyl, wherein the reaction is carried out at a temperature of 60°–120° C.

3. A process according to claim 1, wherein the organic solvent is at least one of a halogenated hydrocarbon, ether, secondary or tertiary alcohol, hydrocarbon, dimethylformamide and methyl isobutyl ketone.

4. A process according to claim 1, wherein 1–5 moles of the carboxylic acid are employed per mole of the halogenobutyric acid ester, and 0.5–1.5 moles of the acid-trapping agent are employed per mole of the carboxylic acid.

5. A process according to claim 1, wherein the organic solvent is at least one of a halogenated hydrocarbon, ether, secondary or tertiary alcohol, hydrocarbon, dimethylformamide and methyl isobutyl ketone, 1–5 moles of the carboxylic acid are employed per mole of the halogenobutyric acid ester, and 0.5–1.5 moles of the acid-trapping agent are employed per mole of the carboxylic acid.

* * * * *